United States Patent
Sadée

(10) Patent No.: US 6,270,979 B1
(45) Date of Patent: *Aug. 7, 2001

(54) METHODS FOR ANTI-ADDICTIVE NARCOTIC ANALGESIC TREATMENTS

(75) Inventor: Wolfgang Sadée, Ross, CA (US)

(73) Assignee: The Regents of the University of California, Oakland, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/200,012

(22) Filed: Nov. 25, 1998

Related U.S. Application Data

(63) Continuation-in-part of application No. 08/447,277, filed on May 22, 1995, now Pat. No. 5,882,944, and a continuation-in-part of application No. 08/703,637, filed on Aug. 27, 1996, now Pat. No. 6,007,986, which is a continuation-in-part of application No. 08/261,500, filed on Jun. 16, 1994, which is a continuation-in-part of application No. 08/081,612, filed on Jun. 23, 1993, said application No. 08/447,277, is a continuation-in-part of application No. 08/261,500.

(51) Int. Cl.[7] .............................. C12Q 1/42; C12Q 1/68; G01N 33/53

(52) U.S. Cl. ........................ 435/7.1; 435/7.2; 435/7.21; 436/501; 514/2

(58) Field of Search .................... 436/501; 435/325, 435/7.1; 514/2

(56) References Cited

U.S. PATENT DOCUMENTS

| | | | |
|---|---|---|---|
| 5,061,715 | 10/1991 | Sunkara et al. | 514/314 |
| 6,007,986 | * 12/1999 | Sadee | 435/6 |

OTHER PUBLICATIONS

Biedler et al., "Morphology and Growth, Tumorigenicity, and Cytogenetics of Human Neuroblastoma Cells in Continuous Culture," *Cancer Research, 33,* pp. 2643–2652 (Nov. 1973).

Costa et al., "Drug Efficacy at Guanine Nucleotide–Binding Regulatory Protein–Linked Receptors: Thermodynamic Interpretation of Negative Antagonism and of Receptor Activity in the Absence of Ligand," *Molecular Pharmacology, 41,* pp. 549–560 (1992).

Frey and Kebabian, "A $\mu$–Opiate Receptor in 7315c Tumor Tissue Mediates Inhibition of Immunoreactive Prolactin Release and Adenylate Cyclase Activity," *Endocrinology, 115*(5), pp. 1797–1804 (1984).

Kogan et al., "Elevated Basal Firing Rates and Enhanced Responses to 8–Br–cAMP in Locus Coeruleus Neurons in Brain Slices from Opiate–Dependent Rats," *European Journal of Pharmacology, 211,* pp. 47–53 (1992).

(List continued on next page.)

Primary Examiner—Michael Borin

(57) ABSTRACT

A method for screening G protein coupled receptors is provided in which G protein coupled receptors that are constitutively active are determined, such as by measuring receptor phosphorylation agonist independent signaling. When a G protein coupled receptor is found to be regulated by constitutive activity, then assay systems may be set up to classify test compounds as agonists, neutral antagonists, or negative antagonists with respect to G protein coupled receptor signaling and phosphorylation. Such determinations and screening are useful for selecting new pharmaceuticals potentially useful in treating disease states mediated by & protein coupled receptors, with applications including treatments in conjunction with narcotic analgesia.

9 Claims, 2 Drawing Sheets

OTHER PUBLICATIONS

Nestler, Eric J., "Molecular Mechanisms of Drug Addiction," *The Journal of Neuroscience, 12(9)*, pp. 2439–2450 (Jul. 1992).

Rasmussen et al., "Opiate Withdrawal and the Rat Locus Coeruleus: Behavioral, Electrophysiological, and Biochemical Correlates," *The Journal of Neuroscience, 10(7)*, pp. 2308–2317 (Jul. 1990).

Sibinga and Goldstein, "Opioid Peptides and Opioid Receptors in Cells of the Immune System," *Ann. Rev. Immunolo., 6,* pp. 219–249 (1988).

Yu et al., "A Human Neuroblastoma Cell Line Expresses $\mu$ and $\delta$ Opioid Receptor Sites," *The Journal of Biological Chemistry, 261,*pp. 1065–1070 (1986).

Abdelhamid and Takemori, "Characteristics of PLUS CODE 83 IS NOT DEFINED and $\delta$ Opioid Binding Sites in Striatal Slices of Morphine–Tolerant and –dependent Mice," *Journal of Pharmacology, 198,*pp. 157–163 (1991).

Sharma et al., Dual Regulation of Adenylate Cyclase Accounts for Narcotic Dependence and Tolerance, *Proc. Nat. Acad. Sci. USA, 72(8)*, pp. 3092–3096 (Aug. 1975).

Saée et al., "Constitutive Activation of the $\mu$–Opioid Receptor: A Novel Paradiagm of Receptor Regulation in Narcotic Analgesia, Tolerance, and Dependence," *Analgesia, 1(1)*, pp. 11–14 (1994).

Lameh et al., "Agonist Induced Conversion of the Hm1 Muscarinic Cholinergic Receptor to a Constitutively Active State: A Novel Papadign of Receptor Regulation," p. 57 of the program for Subtypes of Muscarinic Receptors: The 6$^{th}$ International Symposium, sponsored by Boston University School of Medicine and Johann Wolfgang–Goethe University, held in Fort. Lauderdale, Florida, Nov. 9–12, 1994.

Baker, Mitzi, "New Hypothesis on How Narcotics Produce Tolerance, Dependency," *Synapse*(newspaper of the University of California, San Francisco), 39(15), pp. 1 and 5 (Jan. 12, 1995).

Högger et al., "Activating and Inactivating Mutations in N– and C–terminal i3 Loop Junctions of Muscarinic Acetylcholine Hm1 Receptors," *The Journal of Biological Chemistry, 270(13)*, pp. 7405–7410 (1995).

Wang et al., "Agonist Induced Constitutive Activation of the $\mu$ Opioid Receptor by Phosphorylation," *Regulatory Peptides, 54(1)*, pp. 323–324 (1994).

Yu and Sadée,"Efficacy and Tolerance of Narcotic Analgesics at the Mu Opiod Receptor in Differentiated Human Neuroblastoma Cells," *The Journal of Pharmacology and Experimental Therapeutics, 245(1)*, pp. 350–355 (1988).

Yu et al., "Differentiation of Human Neuroblastoma Dells: Marked Potentiation of Prostaglandin E–Stimulated Accumulation of Cyclic AMP by Retinoic Acid," *Journal of Neurochemistry, 51(6)*, pp. 1892–1899 (1988).

Yu et al., "Regulation of Cyclic AMP by the $\mu$–Opioid Receptor in Human Neuroblastoma SH–SY5Y Cells," *Journal of Neurochemistry, 55(4)*, pp. 1390–1396 (1990).

Schütz and Freissmuth, "Reverse Intrinsic Activity of Antagonists on G Protein–Coupled Receptors," *TiPS, 13,*pp. 376–379 (Oct. 1992).

Chen et al., "Molecular Cloning and Functional Expression of a $\mu$–Opioid Receptor from Rat Brain," *Molecular Pharmacology, 44,*pp. 8–12 (1993).

Wang et al., "Constitutive $\mu$ Opioid Receptor Activation as a Regulatory Mechanism Underlying Narcotic Tolerance and Dependence," *Life Sciences, 54(20)*, pp. 339–350 (1994).

Smith and Loh, "Problems and Approaches in Studying Membrane Opioid Receptors," in *Molecular Approaches to Drug Abuse Research vol. 1: Receptor Cloning, Neurotransmitter Expression, and Molecular Genetics,*ed. Theresa N. H. Lee, pp. 69–84 (1991).

Hawkins et al., "[$^3$H]–[H–D–Phe–Cys–Tyr–D–Trp–Orn–Thr–Pen–Thr–NH$_2$] ([$^3$H]CTOP), A Potent and Highly Selective Peptide for *Mu* Opioid Receptors in Rat Brain," *The Journal of Pharmacology and Experimental Therapeutics, 248(1)*, pp. 73–80 (1989).

* cited by examiner

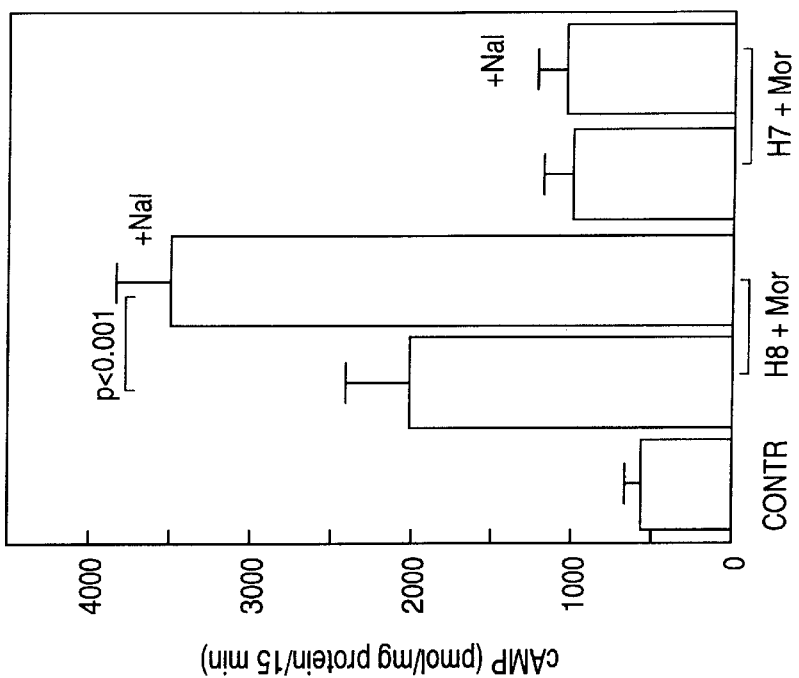
FIG. 3
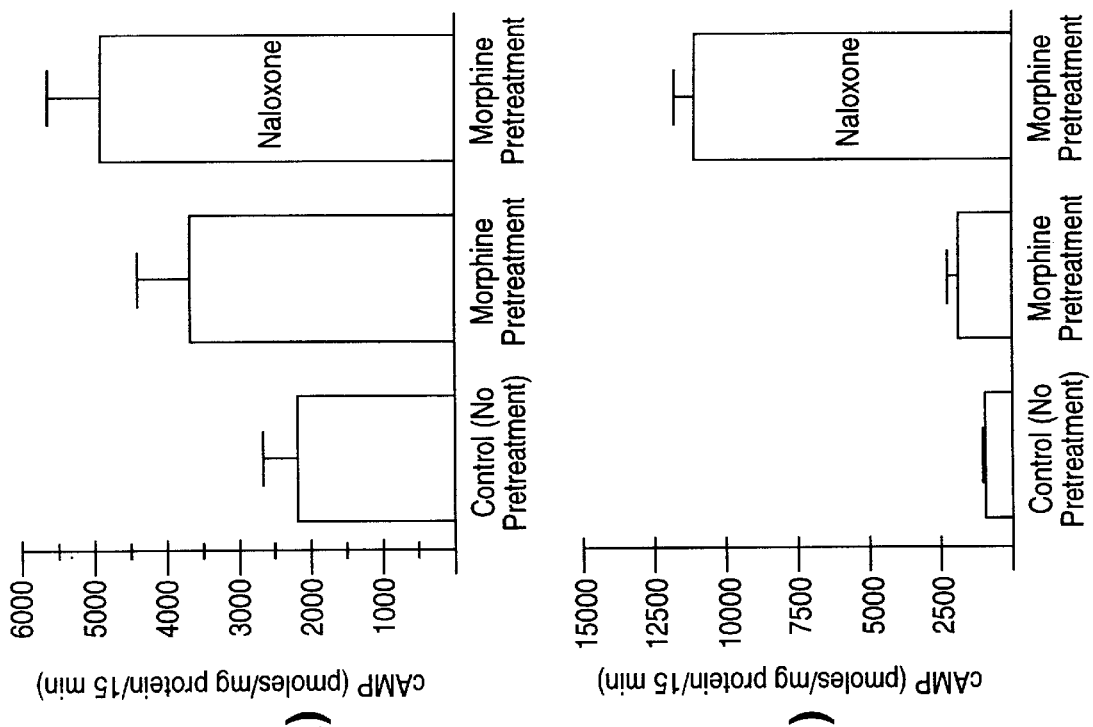
FIG. 2(A)
FIG. 2(B)

METHODS FOR ANTI-ADDICTIVE NARCOTIC ANALGESIC TREATMENTS

This is a continuation-in-part of Ser. No. 08/447,277, filed May 22, 1995, now U.S. Pat. No. 5,882,944, issued Mar. 16, 1999, and of Ser. No. 08/703,637, filed Aug. 27, 1996 now U.S. Pat. No. 6,007,986, both of which were continuation-in-parts of Ser. No. 08/261,500, filed Jun. 16, 1994, itself a continuation-in-part of Ser. No. 08/081,612, filed Jun. 23, 1993, all incorporated herein by reference and all of common assignment herewith.

This invention was made with Government support under Grant Nos. DA 04166 and GM43102, awarded by the U.S. Department of Health and Human Services. The Government has certain rights in this invention.

FIELD OF THE INVENTION

The present invention generally relates to G protein coupled receptors, and more particularly to assays for determining certain activities of G protein receptors, such as opioid $\mu$ receptors, and treatments using anti-addictive agents determinable therefrom.

BACKGROUND OF THE INVENTION

G protein coupled receptors (hereinafter sometimes termed "GPCR"s) comprise a large superfamily of receptors sharing a common structural motif of seven transmembrane helical domains. When a ligand (an agonist) binds to a GPCR and activates it, signal transduction is achieved through the intermediary G protein (a heterotrimeric GTP binding protein) which in turn activates the second messenger system. Although the exact nature of the receptor-G protein interactions is not yet known, the receptor activated regulatory cycle of the G protein involves GTP exchange for GDP, dissociation of the $\alpha$ and $\beta\gamma$ subunits, activation of the second messenger pathway by GTP-$G_{60}$ and $\beta\gamma$, and termination of activation upon GTP hydrolysis to GDP by the inherent GPTase activity of the $\alpha$ subunit. G protein coupled receptors regulate virtually all bodily functions ranging from vision and olfaction to neuronal and endocrine signaling.

A general property of signal transduction mediated by G protein coupled receptors is the attenuation of signaling upon prolonged agonist stimulation. These processes are referred to as desensitization, tachyphylaxis, adaptation, tolerance, or quenching. Because signal attenuation limits the clinical uses of many pharmaceuticals acting on GPCRs, the mechanism for this process has been the focus of much research. Receptor phosphorylation by selective kinases of G protein coupled receptors (termed "GRK"s) has been shown to contribute to desensitization of several receptors. To date, no selective and or potent GRK inhibitors have been reported, other than heparin which does not penetrate into intact cells, even though such inhibitors might prevent desensitization in these cases (e.g., the $\beta 2$ receptor). GRKs selectively polyphosphorylate only the active receptor state, which not only serves as a preferred substrate, but also directly stimulates GRK activity.

Another emerging recognized feature of a number of GPCRs is the presence of a basal level of signaling activity, occurring in the absence of any agonist ligand. Mutations inducing high basal activity have been associated with genetic disorders, demonstrating the physiological relevance of basal receptor activity. For GPCRs displaying basal activity, two classes of antagonist have been defined, i.e., neutral antagonists which block only agonist induced effects without changing basal activity, and inverse agonists, or negative antagonists (or inverse agonists), which also block basal receptor activity.

Prior assay attempts to detect any significant changes of the $\mu$ opioid receptor system during prolonged agonist exposure have been unable to determine biochemical mechanisms underlying narcotic addiction. Thus, much of the current research work has focused on events downstream of the receptor, such as long-term gene regulation, in attempting to account for the dependent-tolerant state. Because tolerance and the dependence liability of narcotic drugs severely limit their clinical utility as potent analgesics and exert a heavy toll on society through illicit narcotic drug use, a screen for agents that could prevent or reverse the narcotic dependent-tolerant state or might facilitate gradual withdrawal would greatly enhance the clinical utility of narcotic analgesics and could serve as an effective pharmacological weapon in the fight against illicit drug use.

SUMMARY OF THE INVENTION

One aspect of the present invention is to provide a means for assaying or measuring the regulation of the addictive state, in the search for compounds that prevent or reverse constitutive $\mu$ receptor activation, and to classify test compounds for their effects on the constitutively active $\mu$ receptor state.

Other aspects of the present invention are methods for treating patients who are addicted to a narcotic analgesic, or who have taken an overdose of a narcotic analgesic, or whose pain is being relieved with a narcotic analgesic. Therapeutic methods in accordance with the invention normally involve selection of an agent with desired effects on the constitutive activation of opioid $\mu$ receptors. These desired effects are determinable from the inventive assays.

Accordingly, practice of the invention is expected greatly to enhance the clinical utility of narcotic analgesics and to serve as effective pharmacological weapons in the fight against illicit drug use.

BRIEF DESCRIPTION OF THE DRAWINGS

FIGS. 2(A,B) graphically illustrate two different types of cells endogenously expressing or stably transfected with the $\mu$ opioid receptor in accordance with the invention; and, FIG. 3 graphically demonstrates how practice of the invention may be applied.

DETAILED DESCRIPTION OF THE PREFERRED EMBODIMENTS

Figure 1:
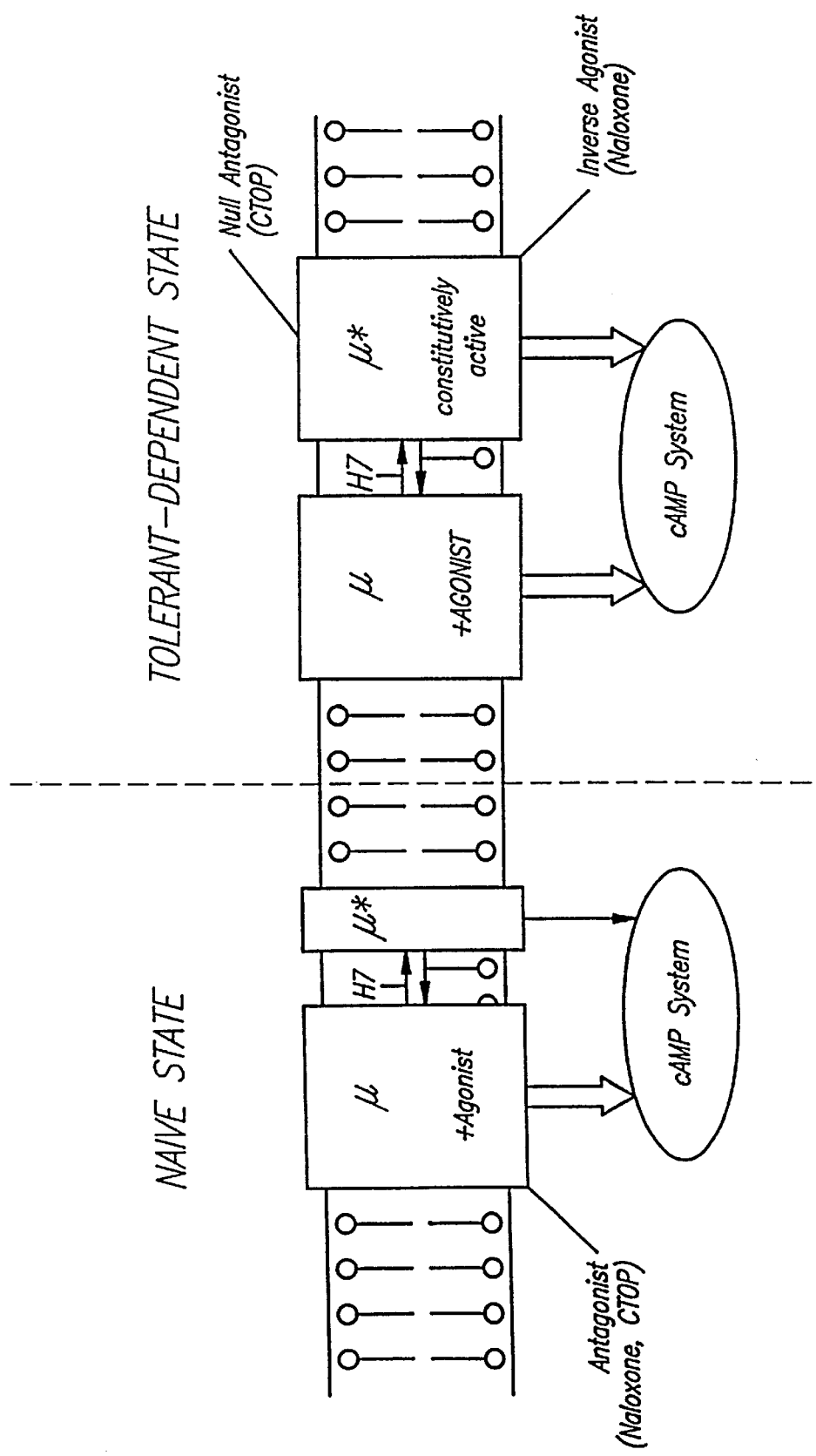
FIG. 1 is a schematic representation of relationships useful in understanding the tolerant dependent state.

The present invention is directed to certain G protein coupled receptors where exposure to agonist leads to persistent or enhanced constitutive activation of the receptors by mechanisms such as phosphorylation.

G protein coupled receptors that are within the scope of this invention include all subtypes of the opioid receptors, but may also be applicable to subtypes of muscarinic, dopamine, adrenergic, cAMP, opsins, angiotensin, serotonin, thyrotropin, gonadotropin, substance-K, substance-P and substance-R receptors, melanocortin, metabotropic glutamate, or any other GPCR receptors known to couple via G proteins.

"Constitutive activation" as used herein means an agonist induced, phosphorylated receptor state which displays continuous signal transduction even after removal of the agonist, and which may be less sensitive to further activation by an agonist. Because many disorders may be mediated by the imbalance of the ratio of agonist activatable receptors to constitutively activated receptors (designed herein as "GPCR/GPCR*"), this ratio may be clinically manipulated in accordance with the invention for therapeutic applications.

The principal novel tenet of the subject invention is that prolonged agonist stimulation and concurrent receptor phosphorylation can cause constitutive activation of some GPCRs, rather than only desensitization. The modified receptor thereby prefers an active state, R*, as if occupied by an agonist, which is distinct from basal activity. A powerful positive feed-forward loop could evolve, by which R* is continuously signaling and simultaneously stimulates its own constitutive activation, e.g. by phosphorylation. As a result, the polyphosphorylated R* can be kept in the active state for prolonged time periods, even though phosphorylation and dephosphorylation steps are fast. Moreover, exposure to agonists enhances formation of R* by further stimulating receptor phosphorylation. This kinetic trapping mechanism represents a novel, potent, long-lasting positive regulatory mechanism with potentially profound and wide-ranging physiological implications. Any receptor undergoing this type of constitutive activation would be expected to contribute dominantly to the overall basal tone in the body, thereby modifying tonicity caused by continuously released hormones and neurotransmitters.

The invention generally relates to the discovery of agonist induced conversion of G protein coupled receptors to a constitutively active, phosphorylated state, R*. In certain G protein receptors, an agonist induces signal transduction and simultaneously induces self-phosphorylation by G protein receptor kinases and related protein kinases which are selective for the activated form of the receptor. While phosphorylation generally leads to receptor desensitization, phosphorylation of this class of G protein coupled receptors leads to constitutive activation. Independent of receptor agonist, constitutively activated GPCRs can transduce signal for a prolonged period of time.

The basis for any assay for constitutive activation of G protein coupled receptors is receptor phosphorylation by the protein kinases critical for constitutive activation and/or the activity of the constitutively active & protein coupled receptors. A non-obvious key element of such an assay is to pretreat the receptor preparation with an agonist, followed by complete removal of the agonist, and subsequently to measure constitutive activity with the use of neutral and negative antagonists (inverse agonists).

One embodiment of this invention is where the receptors are opioid $\mu$ receptors. With reference to FIG. 1 and when using cAMP values as indicia for opioid $\mu$ receptor activity, the constitutively active A receptor is illustrated as "$\mu^*$." That is, the $\mu^*$ receptor represents the constitutively active state of the $\mu$ opioid receptor, whereas $\mu$ is the receptor in its resting state which is sensitive to stimulation by agonists.

The cAMP system consists of a second messenger cascade with G proteins, adenylyl cyclase, and protein kinase A. Activated $\mu$ receptors generally inhibit the cAMP system, and the size of the arrows indicates the relative strength of this inhibition. Thus, the cAMP system may be used to monitor aspects of the invention. In the naive state (no prior drug exposure), the activity of the $\mu^*$ state is minimal, and most receptors are drug sensitive. For purposes of illustration, morphine serves as a prototypal agonist, and naloxone (and CTOP also) as a classical antagonist, i.e., with no pronounced action by themselves but effective in blocking the agonist's effect on the resting $\mu$ state.

During development of the dependent state resulting from narcotic agonist pretreatment, a substantial upregulation of the cAMP system occurs, leading to a cAMP overshoot upon removal of the agonist (here referred to as "spontaneous cAMP overshoot"). In parallel, a slow net conversion of $\mu$ to $\mu^*$ occurs, so that there are fewer $\mu$ receptors remaining sensitive to the action of agonists, as one mechanism leading to tolerance. Further, the increased abundance of the $\mu^*$ state is one of the factors that can compensate for the upregulated cAMP system, to maintain close to normal cAMP levels. Hence, the hallmark of the tolerant-dependent state is the combination of the increased $\mu^*$ activity and the upregulated cAMP system. Naloxone is shown in FIG. 1 to act as an negative antagonist or inverse agonist, i.e., it blocks the $\mu^*$ activity. Hence, the addition of naloxone to drug-free, tolerant-dependent tissue leads to an increased cAMP overshoot (here referred to as "naloxone cAMP overshoot"). In contrast, CTOP acts at the active $\mu^*$ receptor as a neutral or null antagonist by binding to $\mu^*$ without affecting activity.

Returning more broadly to G protein receptors, one simple assay is to measure the constitutive activity of the G protein coupled receptor after pretreatment with (a) agonist alone, (b) agonist and inhibitor of the relevant receptor kinase inhibitor to inhibit R* formation, either in the absence or presence of a neutral or negative antagonist. Because constitutive activation is thought to be mediated by phosphorylation, phosphatase inhibitors should enhance constitutive activation and G protein receptor kinase inhibitors should suppress constitutive activation, if the G protein coupled receptor indeed can be constitutive activated. A variation of this assay is to measure the direct phosphorylation of the G protein coupled receptor instead of the activity of the G protein coupled receptors under conditions that favor the kinase activity relevant to constitutive activation. If negative and neutral antagonist are unknown, screens of known receptor antagonists are required to identify prototypal agents with neutral and negative activity against R*.

Once a G protein coupled receptor is found to be regulated by constitutive activity, assay systems may be set up to screen for compounds with the desired selective properties. For instance, an agonist may be found that activates the GPCR without also inducing the type of receptor phosphorylation relevant to constitutive activation. Such an agonist would prevent the formation of GPCR*.

Morphine is an example of an agonist which induces signal transduction in addition to inducing relevant receptor phosphorylation, which can account for its tolerance and dependence liability. In contrast, the agonist etorphine does not induce the relevant phosphorylation, and it appears to cause also less tolerance and dependence. Moreover, classical antagonists with respect to the GPCR in its ground state (ligands that bind to GPCR with no activity) can be additionally categorized for their simultaneous effects on the constitutively activated GPCRs* (notwithstanding previous classifications of neutral and negative antagonists with regard to basal receptor activity which did not consider receptor phosphorylation).

If it has no effect on GPCRs*, then the antagonist is classified as a null or neutral antagonist. If it blocks the activity of GPCRs*, then the antagonist is classified as a negative antagonist (or inverse agonist). Moreover, these antagonists can also be tested for their ability to suppress continued GPCR* phosphorylation.

As earlier noted, among the G protein coupled receptors that are capable of constitutive activation are the opioid receptors. For example, continuous stimulation of the $\mu$ opioid receptor with morphine results in enhanced conversion to the constitutively active state $\mu^*$, as a principal new mechanism underlying the tolerant-dependent state. Thus, the p opioid receptor system serves as an example for identifying novel agents that affect formation of the constitutively active receptor state and any resultant long-term effects, such as tolerance and dependence to narcotic agonists.

Naloxone is an example of a negative antagonist which blocks constitutive signaling of $\mu^*$, but does not suppress or even enhances continuous $\mu^*$ phosphorylation, as determined by the assays described here. Therefore, naloxone causes immediate and severe withdrawal in the dependent state, but it may fail to reverse the dependent state which continues beyond the duration of naloxone in the body. Therefore, the proposed assays would predict such in vivo properties of antagonist and permit the selection of antagonists that could actively reverse the dependent state by suppressing continuous $\mu^*$ phosphorylation.

Thus, the GPCR/GPCR* ratio can be manipulated by any combination of full agonist, neutral agonist, neutral antagonist, negative antagonist, relevant receptor kinase inhibitor, or phosphatase inhibitor. If an imbalance of GPCR/GPCR* causes a certain disease state, the present invention provides the methods for modulating the GPCR/GPCR* ratio to treating that disease state.

Although the invention will be specifically described using $\mu$ opioid receptors, it may be generalized to any G protein coupled receptor that is capable of constitutive activation upon stimulation with an agonist. G protein coupled receptors that are within the scope of this invention include all subtypes of the opioid, muscarinic, dopamine, adrenergic, cAMP, opsins, angiotensin, serotonin, thyrotropin, gonadotropin, substance-K, substance-P and substance-R, melanocortin, metabotropic glutamate, vasoactive intestinal peptide, secretin, and any other GPCR receptors.

In describing practice of this invention, a source of opioid $\mu$ receptors in combination with a means of monitoring constitutively active $\mu^*$ receptors, such as G protein activity (GTPase activity or GTP exchange) or the cAMP second messenger system, will together sometimes hereinafter be termed the "biological system." One source of opioid p receptors that are exposed to or coupled with cAMP production is a human neuroblastoma (NB) cell line (SK-N-SH) and its NB subclone SH-SY5Y, both which express abundant opioid p receptors (about 50,000 sites per cell). When intact cells are grown under appropriate cell culture conditions, the cells will be producing cAMP. Another source of a useful biological system for purposes of this invention can be certain tissues from experimental animals (e.g. rats and mice, which are good models for opioid $\mu$ receptor activity in humans), such as rat locus coeruleus or guinea pig ileum.

Turning to FIG. 2, cAMP levels in SK-NS-H (subclone SH-SY5Y) neuroblastoma cells (FIG. 2A) and HEK293 cells stably transfected with the )I opioid receptor (FIG. 2B) are illustrated. The first control cAMP level was obtained in untreated cells, whereas the test cells were pretreated with 1 $\mu$M morphine for ~12 hours, followed by complete removal of the agonist. The second cAMP level was then obtained in the absence of any drug, and it represents the known spontaneous cAMP overshoot. The third cAMP level was obtained in the presence of 1 $\mu$M naloxone (IC50 1–3 nM). The difference between the second and third cAMP levels represents the naloxone-induced cAMP overshoot, indicative of the constitutively active $\mu^*$ receptor state.

FIG. 3 demonstrates how this inventive assay can be used to distinguish between an agent capable of preventing $\mu^*$ formation (H7) and an inactive compound (H8). In this experiment, either H7 or H8 (100 $\mu$M) were added to the preincubation medium containing morphine. After removal of the preincubation medium, the second and third cAMP levels were determined as in FIG. 2. Compound H7 abolished the naloxone-induced cAMP overshoot (no difference between the second and the third cAMP value), whereas H8 had no such effect. H7, but not H8, was subsequently found to reverse morphine tolerance and dependence in mice. (Note that H7 and H8 had some effects on the spontaneous cAMP overshoot induced by morphine pretreatment (second cAMP value). This however does not interfere with the evaluation of the naloxone-induced cAMP overshoot which relies on the difference between the second and the third cAMP values.) When whole cells are used as the biological system, then it is desirable to add an adjuvant or stimulating agent of adenylyl cyclase, such as PGE, VIP, or forskolin, which stimulate cAMP production and therefore facilitate assay of the inhibitory effect of the p receptor. The phosphodiesterase inhibitor IBMX is frequently added to further enhance cAMP levels; however, as shown below, IBMX was determined by the assays in this application to be a $\mu$ receptor kinase inhibitor (and hence a prototype of a new class of potential anti-addictive agents); therefore, it must be avoided in the assay. Neuroblastoma cells are preferably first differentiated with, for example, 1–10 $\mu$M retinoic acid to enhance stimulatory and inhibitory receptor coupling to the cAMP system. Such preparations of a biological system have been described by Yu et al., J. Neurochem., 51, pp. 1892–1899 (1988); Yu et al., J. Neurochem., 55, pp. 1390–1396 (1990); and Yu and Sadée, J. Pharmac. Exp. Ther., 245, pp. 350–355 (1988).

A particularly preferred source of opioid $\mu$ receptors that are exposed to or coupled with cAMP production is the HEK293 cell line stably transfected with the $\mu$ receptor gene. However, any cell line that expresses naturally occurring $\mu$ opioid receptors or cloned $\mu$ opioid receptors will work. When intact cells are grown under appropriate cell culture conditions, the cells will be producing cAMP. Another source of $\mu$ opioid receptors are certain tissues from animals such as rat locus coeruleus or guinea pig ileum.

In the opioid system, binding of an agonist (such as morphine) to the $\mu$ opioid receptor leads to the inhibition of adenylyl cyclase which ultimately results in decreased levels of cAMP. Upon prolonged agonist exposure, the cAMP system is upregulated to compensate for the agonist induced inhibition. Ultimately, the effects of the increase numbers of $\mu^*$ receptors and the upregulated cAMP cancel each other out, at least partially. Consequently, a relatively small spontaneous overshoot of cAMP is observed in an agonist exposed receptor system upon the removal of the agonist (hereinafter referred to as the "spontaneous overshoot"). This spontaneous overshoot of cAMP is the difference between the cAMP levels of a dependent receptor system upon the removal of an agonist and the control levels of cAMP in the absence of any agonist, and is one of the accepted biological markers for narcotic dependence. In order to detect constitutive $\mu^*$ activity continuously suppressing cAMP production even after agonist removal, one adds a negative antagonist, such as naloxone (its negative character being defined by the present assays). By suppressing $\mu^*$ inhibitory signaling, naloxone causes an additional cAMP overshoot, referred to here as the naloxone cAMP overshoot, indicative of $\mu^*$ and the dependent state.

Using cAMP as a surrogate measure for receptor activity, one assay embodiment in accordance with the invention involves the measurement of several values. A first cAMP value is optionally, but preferably, determined by measuring the effects of a first portion of receptors on cAMP production in the absence of agonist pretreatment. This first cAMP value acts as a control value. Second and third cAMP values are also determined after agonist pretreatment and agonist removal. The second cAMP value is determined by measuring the effects of a second portion of receptors on cAMP production while the receptors are in a constitutively active state but are substantially free of agonist molecules. The difference between the second cAMP value and the first cAMP value represents the upregulated activity of the cAMP second messenger system, resulting from agonist pretreatment, which is however partially suppressed by $\mu^*$ activity. Presence of such constitutive $\mu^*$ activity represents a novel aspect which had not been suspected previously. The third cAMP value is determined by measuring the effects of a third portion of the receptors on cAMP production while they are in a constitutively active state, are substantially free of any agonist molecules, and are in the presence of a sufficient quantity of a negative antagonist to associate negative antagonist molecules with substantially all the receptors. The difference between the third cAMP value and the second cAMP value represents the activity of the constitutively active $\mu^*$ opioid receptors.

By "substantially free" of agonist molecules is meant that there is less than about 0.1% to about 0.3% of the total agonist drug remaining after pretreatment with a near maximally effective dose so that there would be no measurable effect in response curves. One can make removal determinations through use of radioactively labeled agonist tracer, or radioimmune assays, or one can analyze the wash water for residual agonist by using it to expose naive cells and determining whether there is an agonist effect. Typically, by washing cells carefully three times, substantial agonist removal is accomplished. If one is performing the assay in vivo, then the tissue is removed, sliced, and is washed in a water bath.

Because the conversion of $\mu$ to $\mu^*$ activity is thought to be mediated by phosphorylation, kinase inhibitors should prevent receptor phosphorylation while phosphatase inhibitors should enhance this process. As predicted, these results have been observed in vitro systems. For example, the general kinase inhibitor H7 completely prevents the formation of $\mu^*$ receptors and rapidly reverses $\mu^*$ activity in SH-SY5Y cells. As a result, co-administration of kinase inhibitors with existing analgesics should permit the use of these analgesics without the development of tolerance and dependence. Alternatively, kinase inhibitors should serve as effective agents for treating narcotic addiction.

Suitable G protein receptor kinase inhibitors for practicing the invention in addition to the general kinase inhibitor H7, include the xanthine analog, 3-isobutyl-1-methyl-xanthine (IBMX). Although generally recognized and used as cAMP phosphodiesterase inhibitor (Beavo et al., *Molec. Pharmacol.*, 6, 597 (1971)), IBMX is recognized here for the first time as a $\mu$ receptor kinase inhibitor which suppresses $\mu^*$ formation. Thus, IBMX represents a prototypal agent of a class of drug congeners with broad pharmacological implications, including caffeine, theophylin, theobromine, etc. This invention now permits the selection of alkylated xanthines and congeners with preferential activity against relevant receptor kinases, rather than cAMP phosphodiesterases. Such inhibitors may function as general GPCR kinase inhibitors, and therefore, may also be applicable to other GPCRs that are activatable by GPCR kinases. Alternatively, such kinase inhibitors could also serve to suppress desensitization during drug agonist treatment, for example of the β2 adrenergic receptor, which is thought to desensitize upon phosphorylation.

Finally, direct measurements of $\mu$ receptor phosphorylation can be used. Using the cloned $\mu$ receptor gene transfected into HEK293 cells, phosphorylation of the $\mu$ receptors can be directly measured under conditions that favor the relevant kinase activity. As predicted by the proposed mechanism, the $\mu$ receptor is continuously phosphorylated by $\mu$ receptor kinases (GRKs) because it already preexists in part in the polyphosphorylated $\mu^*$ state and rapidly exchanges phosphate. Moreover, the addition of kinase inhibitor H7 (but not H8), and of IBMX, inhibited $\mu^*$ receptor phosphorylation. Consequently, the direct measurement of $\mu$ receptor phosphorylation can also serve as another screen for compounds that can manipulate the $\mu/\mu^*$ ratio.

Suitable phosphatase inhibitors for practicing the present invention include calyculin-A. Since the PPase-2 selective okadaic acid at a low concentration (15 nM) is ineffective in enhancing $\mu^*$, it appears that PPase-1 is responsible for dephosphorylating $\mu^*$ in SH-SY5Y cells. However, phosphatases may vary in different tissues, and with different receptors.

Accordingly, an inventive assay system can be readily set up to classify compounds for their effects on G protein coupled receptors, such as on the $\mu$ opioid receptors. Using any one or a combination of the markers, cAMP (second messenger system), receptor phosphorylation and relevant receptor kinase activity, compounds may be classified (as agonist, neutral or null antagonist, negative antagonist kinase inhibitors) for their effects both on the agonist activatable $\mu$ receptors and the constitutively active $\mu^*$ receptors. For a more general assay of GPCR signaling, instead of cAMP assays, one can substitute assays of G protein activity, such as GTPase activity or GTP exchange, which represent the more proximal receptor signaling events and are generally applicable to all GPCRs, regardless of their second messenger system.

Using such an assay, compounds may be screened for their selective effects on either the $\mu$ or $\mu^*$ receptors. For instance, agonist for the $\mu$ opioid receptors may be found that do not also have the ability to induce or limit $\mu$ opioid receptor phosphorylation stops relevant to constitutive activation, such as etorphine. Such an agonist would not be expected to induce narcotic tolerance or dependence and would thus be an effective analgesic for treating patients with chronic pain. Similarly, the assay can also be used to screen for compounds that can be used in conjunction with known full agonists (such as morphine) to prevent the development of tolerance and dependence by inhibiting the formation of the constitutively active $\mu^*$ receptors. These compounds may include relevant kinase inhibitors to prevent receptor phosphorylation.

If the goal is to search for compounds to treat a narcotic dependent individual, then the same assays may be used to screen for neutral antagonists that will bind to the agonist activatable $\mu$ opioid receptor to prevent agonist action while at the same time not eliciting the symptoms of withdrawal by blocking the activity of the constitutively active $\mu^*$ opioid receptors. Thus, compounds can be determined that have the properties of blocking the effects of a narcotic analgesic such as morphine or of both morphine and naloxone with no effect when given alone, so as to be considered useful for treating overdoses of narcotic analgesics while avoiding the risk of excessive precipitated withdrawal. This class of compounds should be useful to prevent or reverse the generation of constitutively active receptors and thus can be used therapeutically in conjunction with a narcotic analgesic to suppress the addictive liability of the narcotic analgesic.

Thus, a therapeutic method for treating a patient addicted to a narcotic drug is provided since one can use assays of the invention to select an agent determined to prevent and/or to reverse constitutive activity of opioid receptors and then administer a therapeutically effective amount of the selected agent to the addicted patient. Further, one may treat patients addicted to a narcotic drug, who are suffering from an overdose (or suspected overdose) of the narcotic drug by selecting a neutral $\mu$ receptor antagonist that does not block $\mu^*$ activity. Preferably, the agent selected would also reverse the $\mu^*$ state to the normal $\mu$ receptor state. In another aspect, a therapeutic method for providing analgesia to a patient can comprise selecting a $\mu$ receptor agonist that results in lower conversion of the $\mu$ receptor to its constitutively active state than does a narcotic analgesic such as morphine, and administering such $\mu$ receptor agonist for the treatment for pain, with the desirable properties of reduced tolerance and dependence. Any effect on drug craving cannot yet be predicted from the available results. Yet further, a therapeutic method for providing analgesia to a patient is by selecting a kinase inhibitor and administering a narcotic analgesic in conjunction with the selected kinase inhibitor. The kinase inhibitor selected is effective to retard development of tolerance to and dependence on the narcotic analgesic administered, such as for preventing the formation of constitutively active opioid receptors.

Because the process of constitutive activation lends itself to screening anti-addictive agents and probing the molecular mechanisms of narcotic dependence, practice of the invention is expected to provide a new approach to separating the beneficial activity of narcotics from undesirable long-term effects.

Pharmaceutically effective amounts of agents selected (as by the screening method herein discussed) may be readily determinable clinically by establishing safe dosages and dose-response curves, such as in established clinical pain models. For example, analgesia in rodent animal models can be measured by the tail-flick method of D'Amour and Smith, *J. Pharmac. Exp. Ther.,* 72, pp. 74–79 (1941), and as modified by Tulunay and Takemori, *J. Pharmac. Exp. Ther.,* 190, pp. 395–400 (1974), both incorporated herein by reference. $ED_{50}$ values, their 95% confidence limits, and significance of potency relation between two $ED_{50}$ values may be determined by the method of Litchfield and Wilcoxon, *J. Pharmac. Exp. Ther.,* 96, pp. 99–113 (1949), incorporated herein by reference.

By "narcotic analgesic" as used herein and exemplified by morphine, is meant in addition to morphine, the morphine salts (such as morphine hydrobromide, morphine hydrochloride, morphine mucate, morphine oleate, morphine N-oxide, and morphine sulfate), and morphine analogs such as normorphine, diacetyldihydromorphine, diacetylmorphine hydrochloride, codeine, and diacetylmorphine (heroin). Other widely used narcotic analgesics with which the present invention may be used include alphatrodine, methadone, merperidine, leverthanol, propoxyphene, fentanyl, oxymorphone, anileridine, metopon, and peptides derived from endorphins.

Administration of the selected agent in conjunction with administering a dose of a narcotic analgesic can be within at least about 30 minutes of the narcotic analgesic dose. Preferably, the administering is by administering a singe, admixed dose where the narcotic analgesic is morphine, a morphine analog, or a morphine salt. Thus, administrations maybe intravenous and formulations of pharmaceutically acceptable solutions, carriers, or salts as are well known to the art may be used. Depending upon the agent selected, other forms of administration may be found to be clinically useful.

Moreover, antagonists may be found that block continuous $\mu^*$ phosphorylation by the relevant kinase activity. G protein receptor kinase inhibitors may also be included in the treatment regimen to prevent any further conversion of $\mu$ to $\mu^*$ receptors.

In summary, any combination of agonist, neutral antagonist, negative antagonist, GPCR kinase inhibitors, and phosphatase inhibitors may be used to manipulate the $\mu/\mu^*$ ratio. Because the development of narcotic tolerance and dependence is characterized by the slow conversion of the $\mu$ to $\mu^*$ receptors, most of the compounds for therapeutic benefit are focused on the prevention of the formation of the $\mu^*$ receptors. However, this focus is only with respect to the $\mu$ opioid receptors. In other G protein coupled receptors, it may be desirable to form GPCR* in order to maintain the GPCR/GPCR* at the optimal level. Depending on whether the disease state is mediated by the abundance of one receptor state versus the other, different combinations of agonist, neutral antagonist, negative antagonist, GRK kinase inhibitors, and phosphatase inhibitors will be used. Since the present invention discloses the general mechanism for these G protein coupled receptors, persons skilled in the art will be able to ascertain which combinations of agonist, neutral antagonist, negative antagonist, receptor kinase inhibitors, and phosphatase inhibitors to use to achieve the desired ratio of GPCR/GPCR*.

It is to be understood that the description and the following examples are intended to illustrate and not limit the scope of the invention.

EXAMPLE 1

Because receptor activity is generally regulated by phosphorylation, several known protein kinase inhibitors were tested for their ability to prevent and reverse the formation of the constitutively active $\mu$ receptor state in accordance with the invention, as follows.

The test compounds (10–100 $\mu$M) were first incubated with SK-N-SH cells alone (control) or together with 1 $\mu$M morphine during a 12 hour pretreatment period, followed by washout, no recovery period, and the cAMP assay (see Table 1), to establish the three cAMP values and thereby determine the spontaneous and naloxone induced cAMP overshoot. In a second set of experiments, the test compounds (10–100 $\mu$M) were added to the culture medium during a 30 minute or two hour recovery period. The first set of experiments was designed to identify agents that prevent the naloxone cAMP overshoot (i.e., prevent formation of the active $\mu^*$ state), whereas the second set of experiments was designed to identify agents that reverse the constitutive $\mu$ receptor activation in a short time period.

Among the compounds tested, H7 (1-(5-isoquinolinesulfonyl)-2-methylpiperazine dihydrochloride (10 and 100 $\mu$M)) abolished the naloxone cAMP overshoot when added together with the morphine pretreatment for 12 hours, followed by complete removal of both morphine and H7 drugs. In contrast, H7 pretreatment for 12 hours did not prevent the acute depression of cAMP levels by morphine, showing that it does not interfere with the agonist induced activation of the resting $\mu$ receptor state. Furthermore, when added immediately after the 12 hour morphine pretreatment period, during a recovery period of 30–120 minutes, H7 completely reversed the naloxone cAMP overshoot, i.e. it reversed the constitutively active $\mu^*$ state to the resting $\mu$ state. Other compounds identified as protein kinase inhibitors capable of preventing formation of the constitutively active $\mu$ receptor state are H9 (N-(2-aminoethyl)-5-isoquinolinesulfonamide dihydrochloride), HA-1004 (N(2-guanidinoethyl)-5-isoquinolinesulfonamide hydrochloride), and IBMX.

H7 is known to inhibit several protein kinases including PKA and PKC. Since its closely related agonist, H8 (a kinase PKA-selective inhibitor), fails to block $\mu^*$ function, the relevant kinase activity is uniquely sensitive to H7 only. H7 is a representative of a class of compounds which could prevent and reverse long term narcotic effects by preventing the formation of the constitutively active $\mu$ receptor state but without blocking acute effects. This type of compound may be useful in enhancing the clinical use of narcotic analgesics or in treating narcotic addiction.

EXAMPLE 2

Another focus in practicing the inventive screening is to locate an opioid null antagonist with no ability to reverse the constitutively active $\mu$ opioid receptor state. Whereas naloxone is considered a $\mu$ opioid antagonist (i.e., blocking the activation of the $\mu$ receptor), it is also an inverse agonist, as defined here (i.e., blocking the constitutively active receptor) and illustrated earlier. Hence, its ability to cause severe and immediate withdrawal symptoms is high.

Using SK-N-SH cells, pretreated with 1 $\mu$M morphine for 12 hours, CTOP (D-Phe-Cys-Tyr-D-Trp-Arg-Thr-Pen-Thr-NH$_2$) (1 $\mu$M) was found not to reverse the constitutive activity of the $\mu$ receptor state (i.e., it does not cause the naloxone cAMP overshoot), whereas it has previously been known to fully block the acute effects of morphine. In the inventive cAMP assay system, such a compound is now shown to block the acute effects of morphine, as expected from an antagonist at the resting $\mu$ receptor state, but will also block the inverse agonist effects of naloxone.

To test for these properties of CTOP in the inventive assay, SK-N-SH cells were pretreated for 12 hours with 1 $\mu$M morphine (or with no drug as control) to establish the first and second cAMP values, with no recovery period before the cAMP assay (see Table 1). Then naloxone was replaced by CTOP (1–10 $\mu$M) to determine the third cAMP value. Since the second and third cAMP values were not different, CTOP does not act as an inverse agonist as does naloxone. To test whether CTOP blocks the effects of naloxone, CTOP (1–10 $\mu$M) and naloxone (0.1–1 $\mu$M) were added in combination to the cAMP assay. Reversal of the naloxone cAMP overshoot showed CTOP to act as a neutral (null) antagonist at the active $\mu^*$ state. Further, CTOP (1–10 $\mu$M) also reversed the reduction of the cAMP level caused by morphine (1 $\mu$M), confirming it to act as an antagonist at the resting $\mu$ state. Similar results were obtained with CTOP analog CTAP (D-Phe-Cys-Tyr-D-Trp-Arg-Thr-Pen-ThrNH$_2$).

The selective $\mu$ antagonist CTOP, with a structure completely different from naloxone, is thus a prototypic example of a null antagonist of the $\mu$ receptor, having no effect on the constitutively active $\mu$ receptor state. The potential use of such a null antagonist is twofold. First, it could serve as an antagonist given clinically to counteract narcotic overdose, with the advantage over naloxone that immediate severe withdrawal is avoided (assuming that naloxone induced withdrawal results to a large degree from blocking the constitutive $\mu$ receptor activity). Second, null antagonists may also be useful in treating or inducing treatment of narcotic addiction, for example, in combination with a compound such as H7, to block the vicious circle of the dependent state.

Referring again to FIG. 1, the peptide $\mu$ opioid antagonist CTOP is shown here to act as a null or neutral antagonist at the $\mu^*$ receptor. Therefore, CTOP not only blocks the effects of the agonist morphine at the $\mu$ state, but also the effects of the inverse agonist naloxone at the activated $\mu^*$ state. The therapeutic potential of neutral antagonists is illustrated by the experiment showing CTAP causing significantly less withdrawal in morphine dependent mice and further reduced naloxone induced withdrawal.

EXAMPLE 3

Recently, several laboratories have cloned the $\mu$ receptor gene (e.g. Chan et al., *Molec. Pharmacolo.*, 44, 8–12 (1993)). We have stably transfected the $\mu$ gene into U293 cells (U293-$\mu$~$10^6$ sites/cell), for a more convenient and definitive detection of $\mu^*$ activity for use as a screen for anti-addictive agents. Morphine pretreatment and washout of the drug were the same as described for SH-SY5Y cells. Stimulation of cAMP accumulation in this case was best done with 10 $\mu$M forskolin for 10 minutes. Under these conditions, there was a measurable spontaneous cAMP overshoot after morphine pretreatment; however, the addition of 1–10 $\mu$M naloxone caused a very large additional increase in cAMP levels (up to about 500–600%=naloxone cAMP overshoot, IC:50, 1–3 nM), which indicates the presence of substantial $\mu^*$ activity suppressing cAMP levels. These results show that the narcotic tolerant-dependent state can be reproduced in transfected non-neuronal cells, which can therefore serve as an attractive screening method for identifying anti-additive drugs.

EXAMPLE 4

Regulation of cAMP in Cell Culture

The basic assay is readily adaptable to cell lines or tissue samples SK-N-SH or SH-SY5Y cells as the useful biological systems. The cells were grown at 37° C. in DME H-21 medium supplemented with 10% fetal calf serum containing 100 $\mu$g/ml streptomycin and 100 IU/ml penicillin. Optimal sensitivity to $\mu$ opioid agonist inhibition of cAMP accumulation was observed in retinoic acid pretreated cells (5 $\mu$M for 6 days), and upon adenylyl cyclase stimulation with prostaglandin E$_1$ (PGE$_1$), in the absence of any phosphodiesterase inhibitor.

To induce a tolerant-dependent state, the cells were pretreated with 1 $\mu$M morphine for period ranging from 2 minutes to 48 hours. The relatively low pretreatment concentration of 1 $\mu$M morphine was selected to achieve near maximal effects in tolerant cells while facilitating complete washout of the drug. Immediately before the cAMP accumulation assay, cells were washed twice with medium containing 5% serum and twice more with serum free medium. Supernatants from the washed cells failed to elicit any opioid agonist like cAMP response when transferred to fresh untreated cells, suggesting effective morphine removal during washing. Use of $^3$H-morphine also indicated that 0.1% of the pretreatment concentration was left in the final assay medium, which was below effective morphine levels in this cell line. The values for cAMP levels were determined by radioimmunoassay after stimulation with 1 $\mu$M prostaglandin E$_1$ over 15 minutes in the presence or absence of naloxone.

After pretreatment of SH-SY5Y cells for 6 to 12 hours with morphine, and complete drug removal by thorough washing of the cells, a spontaneous cAMP overshoot was observed when compared to untreated cells. Moreover, addition of naloxone to the pretreated and thoroughly washed, drug-free cells caused a significant additional increase of cAMP accumulation in proportion to the level of tolerance/dependence developed by the cells (this naloxone induced cAMP overshoot ranged from 20 to 80% in over 40 experiments, p<0.001). The difference between the naloxone induced cAMP overshoot and the spontaneous cAMP overshoot represents the activity of the $\mu^*$ receptors in suppressing cAMP levels that is now blocked by the negative antagonist naloxone. Therefore, the naloxone cAMP overshoot provides a novel measure of constitutive receptors' activity observed after agonist pretreatment.

The naloxone cAMP overshoot was also observed in extensively washed membrane homogenates obtained from morphine pretreated cells, further arguing against residual morphine as a cause. Moreover, results with neutral antagonists CTAP and CTOP which do not affect cAMP levels (described below) rule out residual opioids residing at the receptor as the cause for the naloxone cAMP overshoot.

To account for tolerance and dependence, the spontaneous and the naloxone cAMP overshoot should occur gradually. Pretreatment of cells with 1 $\mu$M morphine for 20 minutes or less caused a small decrease of $PGE_1$ stimulated cAMP accumulation, which was not reversed or even enhanced by the addition of naloxone. Therefore, this decrease could not have resulted from residual morphine. Morphine pretreatment longer than 20 minutes caused gradually increasing levels of both the spontaneous and the naloxone cAMP overshoot, until a maximum is reached at 12 hours. A treatment period of 12 hours for maximal cAMP overshoot is compatible with the slow development of tolerance and dependence.

The spontaneous cAMP overshoot disappeared within 30 minutes after morphine removal in this cell line. This result supports the hypothesis that the spontaneous cAMP overshoot is not responsible for the prolonged dependent state. In contrast, the naloxone cAMP overshoot lasted for at least two hours. From 4–12 hours after morphine removal, naloxone had no effect on cAMP levels, in contrast to the decrease in cAMP levels observed in untreated cells. This observation is consistent with the delayed peak of narcotic withdrawal seen in vivo, which occurs after morphine is largely eliminated from the body.

Because many G protein coupled receptors are also linked to the signal pathway via cAMP, the differential ligand effects on cAMP levels can be readily adapted for any particular G protein coupled receptor affecting cAMP. As described above, any cells that are capable of producing cAMP under cell growth conditions (the useful biological system) and that abundantly express either naturally occurring G protein coupled receptors or cloned G protein coupled receptors may be used. Another major second messenger pathway involves turnover of phosphatidyl inositol (PI), e.g., for the muscarinic m1 receptor. The activity of all GPCRs can be assessed by measuring GTPase activity and GTP exchange.

One variation of the assay involves the identification of a negative antagonist as described above. The most efficient method for finding negative antagonists would be to screen known antagonists of the particular G protein coupled receptors for negative intrinsic activity. Antagonists may be identified using standard competition assays that are well known in the art. If the binding of an agonist to the G protein coupled receptors results in increasing the levels of cAMP relative to control levels of cAMP, then compounds that decrease the levels of cAMP relative to control levels of cAMP in the absence of agonist would indicate negative intrinsic (inverse agonist) activity. If the binding of an agonist to the G protein coupled receptors results in decreasing the levels of cAMP relative to control levels of cAMP, then compounds that increase the levels of cAMP relative to control levels of cAMP in the absence of agonist would indicate negative intrinsic activity.

With respect to $\mu$ opioid receptors, the basic assay described in Example 4 can be readily adapted to classify compounds as agonist, negative antagonist, and neutral antagonist depending on their effects on the levels of cAMP.

A full agonist is an agonist that maximally activates signal transduction and induces receptor phosphorylation leading to a slow conversion of $\mu$ to $\mu^*$ receptors upon prolonged exposure. Using the cAMP levels, a full agonist would inhibit cAMP levels and would induce a naloxone induced cAMP overshoot in the dependent state.

In contrast, a novel type of agonist activates only signal transduction but would not induce receptor phosphorylation relevant to constitutive activation. Because there would be no slow conversion from $\mu$ to $\mu^*$ receptors, the naloxone cAMP overshoot would not be observed if naloxone is added to an agonist exposed system in the absence of agonist. Although ideally, such an agonist would be optimal, any agonist that slows the formation of $\mu^*$ receptors relative to such existing analgesics like morphine would also be a therapeutically useful. Etorphine appears to be a prototypal agonist with this novel characteristic.

Antagonists for the $\mu$ opioid receptors may also be additionally classified as either neutral antagonist or negative antagonist depending on their effect on the constitutively activated $\mu^*$ opioid receptors. A neutral antagonist is a classical antagonist with respect to the agonist activatable $\mu$ opioid receptors and does not block the signaling activity of the constitutively active $\mu^*$ opioid receptors. In contrast, a negative antagonist (inverse agonist) is a classical antagonist with respect to the agonist activatable $\mu$ opioid receptors and blocks the signaling activity of the constitutively active $\mu^*$ opioid receptors. Moreover, neutral and negative antagonists can be classified as to their effect on $\mu^*$ phosphorylation. For example, while naloxone is a negative antagonist with respect to signaling, it failed to suppress $\mu^*$ phosphorylation. Therefore, it produces withdrawal, but may not reverse the dependent state.

The $\mu$ selective agonist peptide DAMGO was also tested for its ability to induce signaling and receptor phosphorylation in $\mu$ and epitope-tagged EE$\mu$ receptor transfected HEK293 cells. DAMGO was slightly more potent and efficacious than morphine in both activity tests, when added acutely to the assay incubations. However, in a separate experiment, it was shown that DAMGO, but not morphine induced massive receptor recycling through endocytic vesicles. Since recycling of the $\beta$2 receptor was associated with dephosphorylation, it is possible that during long-term exposure to an agonist such as DAMGO, overall $\mu^*$ formation is lower than with morphine. While this remains to be tested, the distinct downstream effects of morphine and DAMGO demonstrate that different agonists do affect different downstream pathway even at the same receptor.

The ability of the neutral antagonist CTAP to affect $\mu^*$ phosphorylation during the assay incubation was also tested. While CTAP did not block $\mu^*$ phosphorylation, it consistently lowered the level of μ* phosphorylation relative to naloxone. This result suggests that CTAP may affect the balance of μ and μ* receptors in favor of the ground state μ, and therefore, it is potentially useful not only in the treatment of narcotic overdose in addicts, but also as an agent capable of at least partially reversing the tolerant-dependent state.

Classification as either neutral antagonist or negative antagonist can be determined by the addition of the compound to a agonist-free but narcotic dependent cell system (as in Example 5) that has been pretreated with morphine for at least 12 hours. If there is no additional cAMP overshoot above the spontaneous cAMP overshoot, then the compound is a neutral antagonist. If there is an additional cAMP overshoot above the spontaneous cAMP overshoot, then the compound is a negative antagonist.

EXAMPLE 5

Screening for Compounds Using cAMP Levels as a Marker

Using the assay of Example 4, a panel of opioid drugs were classified for their ability to either decrease or increase cAMP levels in morphine pretreated SH-SY5Y cells. As expected from their high potency in causing withdrawal, naloxone, naltrexone, and diprenorphine demonstrated negative intrinsic activity by increasing cAMP levels in drug-free dependent cells. Consequently, naloxone, naltrexone, and diprenorphine were classified as negative antagonists. Buprenorphine, DAMGO and DADLE were classified as full agonists and are either as effective if not more so than morphine. Nalorphine, CTAP and its analogs, CTOP and d-Tic-CTAP were classified as neutral antagonists because they had no significant effect on cAMP levels in dependent cells.

Similarly, the cAMP levels could be used to classify compounds with respect to any particular G protein coupled receptor that transduces signal via the cAMP pathway. If the binding of an agonist to the G protein coupled receptors results in increasing the levels of cAMP relative to control levels of cAMP, then an antagonist that decrease the levels of cAMP relative to control levels of cAMP in the absence of agonist would be a negative antagonist. If the binding of an agonist to the G protein coupled receptors results in decreasing the levels of cAMP relative to control levels of cAMP, then an antagonist that increase the levels of cAMP relative to control levels of cAMP in the absence of agonist would be a negative antagonist. If the antagonist had no effect on the levels of cAMP relative to control levels, then the antagonist would be a neutral antagonist.

Alternatively, measurement of PI turnover could replace cAMP assays where appropriate (m1 receptor). Lastly, direct assays of G protein activity (GTPase and GTP exchange) are universally applicable to all GPCRs. Negative antagonists would suppress, and agonists would enhance G protein activity, while neutral antagonists would be without effect.

A complete agonist, as defined for this invention, with respect to a particular G protein coupled receptor is an agonist that also induces relevant receptor phosphorylation and the resulting slow conversion of GPCR to GPCR*. This may be established by monitoring the levels of cAMP after prolonged exposures to the agonist. The cAMP levels are measured relative to the levels after removal of agonist after prolonged exposure. If there an additive change in the levels of cAMP when a negative antagonist is added, then the agonist is a complete agonist. If there is no additional change or even a subtractive change in the levels of cAMP when a negative antagonist is added, then the pretreatment agonist failed to induce the CPCR* state. A subtractive effect might result if there are significant preexisting basal levels of GPCR*. PI coupled receptors can be analyzed in an analogous fashion, or assays of G protein activities are used.

EXAMPLE 6

Effects of H7 and CTAP in Morphine Tolerant Dependent Mice

Withdrawal

Male ICR mice in groups of 10 each were made acutely dependent on morphine by subcutaneous injection of 100 mg/kg morphine sulfate. After 4 hours, naloxone was given either intraperitoneally or simultaneously by intracerebroventricular and intrathecal injections to induce withdrawal. Alternatively, CTAP was injected. To test the ability of kinase inhibitors to reverse the dependent state, animals were injected 3.5 hours after the first 100 mg/kg morphine dose with saline or with H7 or H8. At 4 hours, withdrawal was precipitated by injection of naloxone (3 mg/kg intraperitoneally). Mice were then placed in Plexiglass cylinders and observed for a 15 minute period with the number of vertical jumps recorded.

Tolerance

Mice in groups of 10 were again injected subcutaneously with 100 mg/kg morphine sulfate, and analgesia was measured with the tail immersion assay at 55° C. by determining the time elapsed before the tail is flicked (15 seconds cutoff=100% analgesia). At 4.5 hours after the first dose, either saline alone or saline containing 50 nM H7 was injected. At 5 hours after the analgesic effect of first morphine dose had essentially ceased and a second dose of 10 mg/kg morphine sulfate was injected to determine the degree of tolerance.

Results

The formation of μ* can account for narcotic dependence, and paradoxically also for tolerance. Assuming that all μ receptors were converted to μ*, it follows that further addition of an agonist would be without effect, because all receptor are already active, and the organism is adapted to this activity. If μ* activity were responsible for narcotic tolerance and dependence, then the following effects in morphine pretreated animals would be predicted. First, H7 should reverse tolerance and suppress naloxone induced jumping without affecting morphine analgesia whereas H8 should be without any effect. Second, the neutral antagonist CTAP should cause less withdrawal than naloxone because it does not reverse the activity of μ*. Finally, CTAP should reverse naloxone induced jumping.

Administration of H7 30 minutes before naloxone strongly suppressed the number of naloxone precipitated jumps without affecting gross behavior of the animals or morphine antinociception as measured in the 55° C. hot water tail-flick test. In contrast, H8 was without effect on naloxone induced jumping. Therefore, the protein kinase inhibitor H7 reversed the drug dependent state towards the naive state within 30 minutes. H7 also fully reversed morphine tolerance observed 5 hours after a 100 mg/kg morphine sulfate dose in mice. The test dose of 10 mg/kg morphine sulfate produced only 22±14% analgesia in the tail flick assay when given 5 hours after the first dose, and 30 minutes after a control injection of saline. However, injection of 50 nM H7 30 minutes before the second morphine test dose completely reversed tolerance yielding 90±10% analgesia. Therefore, H7 reversed both morphine tolerance and dependence in an acute mouse model as predicted.

As expected for a neutral antagonist, CTAP caused significantly less withdrawal jumping, from 77±20 jumps for naloxone to 32±12 jumps, and it partially reversed naloxone induced withdrawal jumping. These combined results document that the predictions from the in vitro results can be verified in an animal model of narcotic tolerance and dependence. This is the first time that agents have been successfully used to reverse tolerance and dependence, selected on the basis of a novel mechanism of μ receptor phosphorylation and constitutive activation.

EXAMPLE 7

Direct Measurement of μ Receptor Phosphorylation
Epitope-tagged μ opioid receptor (EE-μR)

The sequence, TTTTAAGCTT ACCATGGAAT ACAT-GCCAAT GGAAGACAGC AGCACCGGCC CAGGG (SEQ ID NO: 1), containing a HindIII restriction site, the start codon, and a sequence encoding the epitope EYMPME (underlined portion), served as the 5' primer in order to append the epitope tag to the amino terminal of the rat μ receptor by the polymerase chain reaction. The 3' primer sequence, GCTCTAGAGC GAGGGTCTGG ATGGTG (SEQ ID NO: 2), contained a stop codon and an XbaI restriction site. The amplified fragment (EE-μR) was ligated into pRc/CMV which contains a neomycin-resistance gene, and subcloned into the E. coli TOP 10F' strain. The 5' sequence containing the epitope was verified by automated sequencing. Human embryonic kidney cells (HEK293) were transfected by the calcium phosphate method, and clonal cell lines stably expressing EE-μR were selected with 400 μg/ml G-418 and maintained in DMEM/H-16/F-12 with 10% fetal calf serum and 200 μg/ml G-418.

Ligand Binding Assays and cAMP assay

EE-μR expression was quantified with [3H]-diprenorphine. HE293 cells stably expressing EE-μR were harvested in PBS, and triplicate samples were incubated with 10 nM [$^3$H-diprenorphine and differing concentrations of diprenorphine or morphine sulfate in 50 mM Tris, pH 7.4. Cells were incubated for 2 hours at 20° C. and harvested on GF/C glass filters which were washed three times with cold PBS, and the tritium content determined. Displacement data were fit to the logistic function, $B=B_{max}-[B_{min}*L]/[IC_{50}+L]+NSB$, where B is the tracer bound, L=diprenorphine or morphine concentration, and NSB is the nonspecific binding. Protein content was determined by the Bradford method. Bradford, *Anal. Biochem.*, 72, pp. 248–254 (1976).

Immunoprecipitation of the Phosphorylated EE-μR

Phosphorylation of EE-μR was performed in permeabilized cells by a modification of the procedure described by Raymond. Raymond, *J. Biol. Chem.*, 266, pp. 14747–14753 (1991). Confluent flasks with approximately 2×10$^7$ HEK293 cells were washed gently in 50 mM Tris (pH 7.4), 100 mM NaCl and incubated for 15 minutes at 37° C. in phosphate-free DMEM. After harvesting and brief centrifugation cell pellets were resuspended in phosphate-free medium and aliquots of digitonic were added until approximately 90% of cells were permeabilized as defined by failure to exclude trypan blue dye. Final digitonine concentration was 150–200 μM. Cells were treated with 10 μM morphine sulfate and/or buffer and 1 μCi/μl[γ-$^{32}$P]-ATP in a final volume of 500 μl for 15 minutes at 25° C. with gentle rocking. Labeling medium was removed and cell pellets were washed twice in ice cold Tris-NaCl buffer containing phosphatase and protease inhibitors (50 mM Tris, pH 7.4, 100 mM NaCl, 10 mM sodium pyrophosphate, 10 mM NaF, 1 mM benzamidine, 1 μg/ml leupeptin, and 1 μg/ml aprotinin). Cells were resuspended in ice-cold lysis buffer containing phosphatase inhibitors, incubated on ice for 10 minutes, and homogenized in a Dounce homogenizer. A membrane pellet was prepared, solubilized in 10 mM CHAPS, and immunoprecipitated with 1:40 dilution of anti-EE monoclonal antibody. The incorporation of $^{32}$P into the supernatant was determined at the time of immunoprecipitation of equalized control and transfected samples. The 8% SDS-PAGE gels were autoradiographed and bands were quantified by scanning densitometry.

Results

The epitope-tagged EEm receptor was similar to the wild-type μ receptor in all pharmacological assays. Confirming predicted results, the epitope tagged μ opioid receptor is significantly phosphorylated in the absence of any agonist under the incubation conditions used (presence of $Ca^{++}$ and $Na^+$), suggesting the presence of μ*. Agonist exposures (15 minutes) during the labeling assay increased the levels of phosphorylation of the receptors by nearly twofold. Moreover, pretreatment with 1 μM morphine for 6–12 hours, followed by agonist removal before the phosphorylation assay, enhanced μ receptor phosphorylation by threefold, indicative of agonist dependent conversion of μ to μ*. Naloxone did not block μ receptor phosphorylation, but in contrast appeared to slightly stimulate it. This result is consistent with the finding that naloxone does not reverse the dependent state in vivo. As predicted GRK kinase inhibitor H7 strongly inhibits μ receptor phosphorylation, either when added acutely to the assay, or via pretreatment and subsequent removal before the assay. This result suggest that μ receptor kinase inhibition depletes the μ* state.

As a result, assays may be modified to use direct receptor phosphorylation as a marker for classifying compounds as a agonist, negative antagonist, and neutral antagonist with respect to stimulating receptor phosphorylation, and receptor kinase inhibitor. Although these results are with respect to the μ opioid receptors, they may be readily modified for any particular G protein coupled receptor. Moreover, receptor kinase inhibitors may be found directly using standard enzyme activity assays. See generally, Chen et al., *J. Biol. Chem.*, 268: 7825–7831 (1993).

There are at least 7 genes encoding the family of related G protein receptor kinases that all have the same characteristics essential for supporting the positive feed-forward mechanism of sustained GPCR* activity. These are expressed differentially in different tissues, providing the opportunity for selective effects; however, no selective inhibitors are available. However, distinct other kinases are also likely to be relevant to constitutive activation. This invention permits the selection of such kinase inhibitors and their evaluation as potential therapeutic agents.

Mental disorders involving the dopaminergic system include schizophrenia and Parkinsonism, which are associated with an excess and deficit, respectively of dopaminergic transmission. Moreover, dopaminergic pathways are thought to be essentially involved in reward mechanisms and drug cravings. However, the mechanisms underlying these processes are not understood.

As with the μ opioid receptors which involve narcotic tolerance and dependence, an imbalance of the agonist activatable dopamine receptor (DR) and constitutively active dopamine receptors (DR*) may be involved in schizophrenia, Parkinsonism, and drug cravings. Excess constitutively active dopamine receptor activity could be involved in schizophrenia, and drug seeking behavior/addiction. As an example, constitutive activation of the dopamine receptors could also explain why treatment of Parkinsonism with L-DOPA (which gets converted to dopamine) loses its effectiveness. Thus, in a manner analogous to the coadministration of a kinase inhibitor with a narcotic analgesic to prevent or to retard the development of tolerance, the coadministration of a dopamine receptor kinase inhibitor with L-dopa is believed useful in treating Parkinsonism, to prevent or retard the constitutively active state of dopamine receptors. Therefore, analogous to the results with the $\mu$ opioid receptors, manipulating the DR/DR* ratio could lead to treatment of schizophrenia and drug addiction, and to enhance existing therapies for Parkinson's disease.

Among the known dopamine receptor subtypes, the D2 receptor plays a prominent role in schizophrenia. Changes in D2 ligand binding characteristics that were observed in post-mortem CNS tissue from schizophrenic patients, have suggested that altered receptor-G protein coupling may play a role. Preliminary experiments analogous to those initially performed for the $\mu$ opioid receptors in stably transfected HEK293 cells, indicate that D2 receptors are also regulated through constitutive activation. While quinpirole served as the agonist (equivalent to morphine), haloperidol, thuphenazine, trifluoperatine, spiperone, and sulpiride all displayed some degree of negative antagonism. Spontaneous and negative antagonist induced cAMP overshoots were observed after quinpirole pretreatment and thorough drug removal by washing. This result supports the view that basal activity of the D2 receptor can also be further enhanced during agonist exposure. To determine D2 receptor phosphorylation, the same EE epitope tag was introduced into the D21 gene (long splice isoform), immediately adjacent to the ATG initiation codon. Thus, a similar set of assays can now be performed with the D21 receptor.

EXAMPLE 8

Using HEK293 cells stably transfected with the long splice isoform of the D2 receptor, incubation with a known antagonist, spiperone in the absence of agonist, resulted in decreased cAMP levels relative to control indicating intrinsic negative activity, as proposed for the $\mu$ receptor. The effects of the agonist quinpirole and antagonist spiperone on cAMP levels before and after pretreatment with quinpirole were similar to that of morphine and naloxone in the $\mu$ opioid receptor system. Because the D2 receptor also transduces signal via the cAMP pathway, assays described for the $\mu$ opioid receptor system may thus be readily adapted for the D2 receptor.

As cholinergic pathways intimately associated with cognitive functions, cholinergic deficits are a hallmark of neurodegenerative disorders involved with memory impairment. Elevation in levels of acetylcholine are thought to enhance cognitive functions by postsynaptic action on the muscarinic m1 receptor. The muscarinic m1 receptor is coupled to phospholipase C which in turn stimulates phosphatidyl inositol (PI) turnover. One example of the attempt to modulate levels of acetylcholine for therapeutic benefit is tacrine, an acetylcholinesterase inhibitor, for the treatment of Alzheimer's disease.

EXAMPLE 9

An extensive study of the m1 receptor which includes nearly 100 mutations of the m1 receptor gene has been undertaken in an effort to understand m1 signal transduction and regulation. One mutant, m1-E360A, was found to be a partially activated receptor and was stably transfected into HEK293 cells for further studies. Because of its partial activity, m1-E360A in HEK293 cells has a basal activity for stimulating PI turnover significantly above background.

The availability of this mutant form of the m1 receptor facilitated finding negative antagonists. Because of their decreasing effects on m1-E360A basal activity, atropine and scopolamine were found to be negative antagonists. As expected if constitutive activity were due to phosphorylation, pretreatment with agonist carbochol and with the phosphatase inhibitor calyculin A enhanced the basal activity. Therefore, HEK293 cells transfected with the m1 wild-type or the activating mutant E360A can serve in the assays equivalent to those described for the $\mu$ receptor.

EXAMPLE 10

Depending on the particular condition to be treated, it will be desirable to either increase or decrease the formation of the constitutively active GPCR*. In either case, any combination of agonist, neutral antagonist, negative antagonist, GRK kinase inhibitor, and phosphatase inhibitor may be used to obtained the desired effect. The classification of the compounds as agonist, neutral antagonist, negative antagonist, each with respect to signaling and phosphorylation, GPCR kinase inhibitor, or phosphatase inhibitor, can be achieved by the methods discussed in prior examples. For example, practice of the present invention may yield agonists that would transduce the desired signal but without the resulting constitutive activation of the receptors. If known agonists are to be used that stimulate both signaling and phosphorylation, they may be used in combination with receptor kinase inhibitor to prevent the formation of the constitutively active receptors. If attenuation of constitutive activity is sought to be treated, neutral antagonist and/or receptor kinase inhibitors may be used. However, if the goal is to form constitutively active GPCR*, then full agonist and/or phosphatase inhibitors may be used. Because the present invention discloses the general mechanism for these G protein coupled receptors, persons skilled in the art would know which combination of agonist, neutral antagonist, negative antagonist, GPCR kinase inhibitor, or phosphatase inhibitor should be used to achieve the desired result. Useful agents can be selected with the described assays.

EXAMPLE 11

3-Isobutyl-1-methylxanthine (IBMX) is commonly used during cAMP assays (at a concentration of 500 $\mu$M) to inhibit cAMP breakdown by the enzyme cAMP-phosphodiesterase. Thereby, one increases the levels of cAMP accumulating during the assay. A direct measurement of $\mu$ receptor phosphorylation, using the epitope tagged $\mu$ receptor gene and the $^{32}$P labeling assay, was conducted by techniques analogous to those already described. IBMX at 100 $\mu$M, suppressed $\mu$ receptor phosphorylation as observed for H7.

Thus, IBMX is active in preventing receptor phosphorylation and appears to be an inhibitor of the $\mu$ receptor kinase(s). This is of general importance, as this activity may also apply to receptors other than the $\mu$ opioid receptor (e.g., the dopamine or muscarinic receptors). Moreover, IBMX is an alkylated xanthine, and thus, a prototype of a family of important drugs and chemicals, including theophylline, caffeine, theobromine. Among these one may find congeners with enhanced selectivity for the receptor kinases over phosphodiesterases. Such an agent could be effective in the treatment of drug addiction, and other diseases that may be associated with elevated basal levels of receptor activity because of receptor phosphorylation.

It is to be understood that while the invention has been described above in conjunction with preferred specific embodiments, the description and examples are intended to illustrate and not limit the scope of the invention, which is defined by the scope of the appended claims.

It is claimed:

1. An in vitro method of screening a test compound for effects on opioid µ receptors, comprising:

providing cells having opioid µ receptors, the receptors having been pretreated by having been incubated with a narcotic analgesic functioning as an agonist therein for about 12 hours or longer, and then subsequently removing the narcotic analgesic so that the receptors are substantially free of narcotic analgesic, the receptors having a first receptor activity determined therefrom:

determining a second receptor activity while the receptors are substantially free of narcotic analgesic, the second receptor activity determined in the presence of an inverse agonist associated with substantially all the receptors;

determining a third receptor activity by contacting a test compound with the receptors having had the narcotic analgesic substantially removed therefrom; and, comparing the receptor activities.

2. The method as in claim 1 wherein the narcotic analgesic is morphine, and the inverse agonist is naloxone.

3. The method as in claim 1 wherein the cells are SK-N-SH or HEK293 cells transfected with the µ opioid receptor gene.

4. The method as in claim 1 wherein the determining of receptor activity includes measuring phosphorylation of the receptors.

5. The method as in claim 1 wherein the determining of receptor activity includes measuring phosphatidyl inositol levels.

6. The method as in claim 1 wherein the determining of receptor activity includes measuring GTPase activity.

7. The method as in claim 1 wherein the determining of receptor activity includes measuring GTP exchange.

8. The method as in claim 1 wherein the determining of receptor activity includes measuring an activity of a G protein coupled receptor kinase.

9. The method as in claim 1 wherein the comparing of receptor activities includes classifying the test compound as an agonist, neutral antagonist, or a negative antagonist.

* * * * *